US008859243B2

(12) United States Patent
Okutani et al.

(10) Patent No.: US 8,859,243 B2
(45) Date of Patent: Oct. 14, 2014

(54) METHOD FOR PRODUCING AN L-AMINO ACID

(75) Inventors: Satoshi Okutani, Kawasaki (JP); Shinya Fujiki, Kawasaki (JP); Shintaro Iwatani, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 806 days.

(21) Appl. No.: 12/419,409

(22) Filed: Apr. 7, 2009

(65) Prior Publication Data

US 2009/0239268 A1 Sep. 24, 2009

Related U.S. Application Data

(63) Continuation of application No. PCT/JP2007/067440, filed on Sep. 6, 2007.

(30) Foreign Application Priority Data

Oct. 10, 2006 (JP) .................................. 2006-276659

(51) Int. Cl.
*C12P 13/04* (2006.01)
*C12P 13/22* (2006.01)
*C12P 21/02* (2006.01)
*C12N 1/22* (2006.01)
*C12N 1/20* (2006.01)

(52) U.S. Cl.
CPC ............... *C12P 13/04* (2013.01); *C12P 13/222* (2013.01); *C12P 21/02* (2013.01); *C12P 13/227* (2013.01); *C12N 1/22* (2013.01); *C12N 1/20* (2013.01)
USPC ............................. 435/108; 435/115; 435/116

(58) Field of Classification Search
CPC ............................. C12P 13/227; C12P 13/22
See application file for complete search history.

(56) References Cited

U.S. PATENT DOCUMENTS

| 4,675,339 | A | 6/1987 | Inoue et al. |
| 5,168,056 | A | 12/1992 | Frost |
| 5,618,716 | A | 4/1997 | Burlingame |
| 5,763,230 | A | 6/1998 | De Hollander et al. |
| 5,763,231 | A | 6/1998 | Ono et al. |
| 5,776,736 | A | 7/1998 | Frost et al. |
| 5,776,740 | A * | 7/1998 | Hatakeyama et al. ........ 435/108 |
| 5,856,148 | A | 1/1999 | Burlingame |
| 5,906,925 | A | 5/1999 | Liao |
| 5,912,113 | A | 6/1999 | Nakamura et al. |
| 5,985,617 | A | 11/1999 | Liao |
| 6,025,169 | A | 2/2000 | Nakamura et al. |
| 6,180,373 | B1 | 1/2001 | Wich et al. |
| 6,319,696 | B1 | 11/2001 | Kishino et al. |
| 6,489,100 | B1 | 12/2002 | Liao |
| 6,596,517 | B2 | 7/2003 | Izui et al. |
| 6,653,110 | B2 | 11/2003 | Sato et al. |
| 6,960,455 | B2 | 11/2005 | Livshits et al. |
| 7,045,320 | B2 | 5/2006 | Iwatani et al. |
| 7,294,491 | B2 | 11/2007 | Ueda et al. |
| 7,300,776 | B2 | 11/2007 | Ito et al. |
| 7,306,933 | B2 | 12/2007 | Van Dien et al. |
| 7,319,025 | B2 | 1/2008 | Ueda et al. |
| 2003/0148473 | A1 | 8/2003 | Livshits et al. |
| 2003/0157667 | A1 | 8/2003 | Vitushkina et al. |
| 2005/0191684 | A1 | 9/2005 | Zimenkov et al. |
| 2006/0035348 | A1 | 2/2006 | Gulevich et al. |
| 2006/0281945 | A1 | 12/2006 | Kushiku et al. |

FOREIGN PATENT DOCUMENTS

| EP | 0 837 134 A2 | 4/1998 |
| EP | 0 837 134 A3 | 4/1998 |
| EP | 1 078 989 | 2/2001 |
| EP | 1 270 721 | 1/2003 |
| FR | 2 669 935 | 6/1992 |
| JP | 62-000288 | 1/1987 |
| JP | 62-288 | 1/1987 |
| JP | 5-76463 | 10/1993 |
| WO | WO95/33843 | 12/1995 |
| WO | WO03/044191 | 5/2003 |
| WO | WO03/048374 | 6/2003 |
| WO | WO2005/103275 | 11/2005 |

OTHER PUBLICATIONS

U.S. Appl. No. 12/184,637, Imaizumi et al, filed Aug. 1, 2008.*
U.S. Appl. No. 11/877,726, Van Dien et al, filed Oct. 24, 2007.*
U.S. Appl. No. 12/055,438, Iwatani et al, filed Mar. 26, 2008.*
Provisional U.S. Appl. No. 61/154,500, Iwatani et al, filed Feb. 23, 2009.*
International Preliminary Report on Patentability for PCT Patent App. No. PCT/JP2007/067440 (Apr. 30, 2009).
Internation Search Report for PCT Patent App. No. PCT/JP2007/067440 (Oct. 16, 2007).
Supplementary European Search Report for EP Patent App. No. 07806881.4 (Dec. 28, 2011).

* cited by examiner

*Primary Examiner* — Allison Fox
(74) *Attorney, Agent, or Firm* — Shelly Guest Cermak; Cermak Nakajima McGowan LLP

(57) ABSTRACT

The present invention provides a method for producing an L-amino acid by fermentation by culturing a microorganism having an L-amino acid-producing ability in a liquid medium to precipitate the L-amino acid, wherein a polymer such as a water-soluble cellulose derivative, a water-soluble polyvinyl compound, a polar organic solvent-soluble polyvinyl compound, a water-soluble starch derivative, an alginic acid salt, and a polyacrylic acid salt is added to the medium.

9 Claims, No Drawings

METHOD FOR PRODUCING AN L-AMINO ACID

This application is a continuation of PCT/JP2007/067440, filed Sep. 6, 2007, which claims priority under 35 U.S.C. §119 to Japanese Patent Application No. 2006-276659, filed on Oct. 10, 2006, which is incorporated in its entirety by reference. The Sequence Listing in electronic format filed herewith is also hereby incorporated by reference in its entirety (File Name: US-393_Seq_List; File Size: 1 KB; Date Created: Apr. 7, 2009).

BACKGROUND OF THE INVENTION

1. Technical Field

The present invention relates to a technique useful in the fermentation industry, that is, a method for efficiently producing an L-amino acid, especially hydrophobic amino acids, and L-threonine and L-glutamic acid, by fermentation using a microorganism. Hydrophobic L-amino acids are useful as components of nutrient mixtures for medical care. Furthermore, these amino acids are useful in various ways as additives for animal feed and reagents in the drug industry and chemical industry. Moreover, L-phenylalanine is also useful as a raw material in sweeteners. Furthermore, L-threonine is useful for animal feed, and L-glutamic acid is widely used as a raw material in seasonings, etc.

2. Background Art

L-amino acids are industrially produced by fermentation using coryneform bacteria or Enterobacteriaceae which are able to produce amino acids. Bacterial strains isolated from the nature or artificial variants of such strains, recombinant strains with recombinantly enhanced L-amino acid biosynthesis enzymes, and so forth are used to improve the productivity.

Examples of strains which are able to produce the hydrophobic amino acid L-tryptophan by fermentation include strains with enhanced activity of one or more enzymes such as anthranilate synthase, phosphoglycerate dehydrogenase, and tryptophan synthase (WO94/08031), and strains transformed with the tryptophan operon (Japanese Patent Laid-open (Kokai) Nos. 57-71397 and 62-244382, U.S. Pat. No. 4,371,614).

Furthermore, for L-glutamic acid fermentation, Japanese Patent Laid-open No. 63-214189 discloses a technique for increasing L-glutamic acid-producing ability by amplifying genes encoding glutamate dehydrogenase (gdh), isocitrate dehydrogenase (icdA), aconitate hydratase (acnA, acnB), and citrate synthase (gltA).

Furthermore, for L-threonine fermentation, Japanese Patent Laid-open No. 2001-346578 discloses an L-threonine-producing bacterium in which the aspartokinase III gene (lysC), aspartate semialdehyde dehydrogenase gene (asd), aspartokinase I gene (thrA), homoserine kinase gene (thrB), and threonine synthase gene (thrC), which are all encoded by threonine operon, are enhanced.

L-amino acid productivity has been considerably increased by the aforementioned breeding of microorganisms or improvement of production methods. However, in order to respond to further increases in demand in the future, the development of methods which provide more efficient production of hydrophobic L-amino acid at a lower cost are still necessary, and therefore, still represent a need in the art.

A method of performing fermentation by crystallizing the L-amino acid which accumulates in the culture medium is known (Japanese Patent Laid-open No. 62-288, European Patent Publication No. 1078989). The purpose of this method is to maintain a constant concentration of the L-amino acid in the culture medium by precipitating the L-amino acid into the culture medium.

Furthermore, a method of producing L-glutamic acid by using a microorganism which can produce L-glutamic acid by precipitation of L-glutamic acid is disclosed (U.S. Pat. No. 6,905,819).

Furthermore, as a method for crystallizing a hydrophobic L-amino acid, the method of purifying an L-amino acid by using a water-soluble cellulose derivative is known (Japanese Patent Publication (Kokoku) No. 5-76463). However, there have been no reports to date of a method of performing fermentation with precipitation of L-amino acids, wherein the L-amino acid precipitates in the medium and productivity of the L-amino acid is improved by adding a polymer such as a water-soluble cellulose derivative to the medium.

SUMMARY OF THE INVENTION

An aspect of the present invention is to improve productivity of L-amino acid or purity of L-amino acid in L-amino acid crystals in the production of the L-amino acid by fermentation.

It has been found that by adding a polymer such as water-soluble cellulose derivatives, polyvinyl compounds, water-soluble starch derivatives, alginic acid salts, and polyacrylic acid salts to a fermentation medium, productivity of an L-amino acid can be improved, and impurities in the crystals of the L-amino acids which precipitate in the medium can be reduced.

It is an aspect of the present invention to provide a method for producing an L-amino acid by fermentation comprising A) culturing a microorganism which is able to produce an L-amino acid in a liquid medium so that the L-amino acid precipitates into the medium, wherein the medium contains a polymer selected from the group consisting of a water-soluble cellulose derivative, a water-soluble polyvinyl compound, a polar organic solvent-soluble polyvinyl compound, a water-soluble starch derivative, an alginic acid salt, and a polyacrylic acid salt, and B) collecting the L-amino acid from the medium or the microorganism.

It is a further aspect of the present invention to provide the aforementioned method, wherein the polymer is selected from the group consisting of carboxymethylcellulose, methylcellulose, sodium carboxymethylcellulose, hydroxypropylcellulose, hydroxypropylcellulose phthalate, polyvinylpyrrolidone, polyvinyl alcohol, polyvinylacetal diethylaminoacetate, sodium arginate, and sodium polyacrylate.

It is a further aspect of the present invention to provide the aforementioned method, wherein the microorganism is a bacterium belonging to the family Enterobacteriaceae or a coryneform bacterium.

It is a further aspect of the present invention to provide the aforementioned method, wherein said bacterium belongs to the genus *Escherichia* or genus *Pantoea*.

It is a further aspect of the present invention to provide the aforementioned method, wherein said L-amino acid is selected from the group consisting of L-leucine, L-isoleucine, L-valine, L-tryptophan, L-phenylalanine, L-tyrosine, L-threonine, and L-glutamic acid.

It is a further aspect of the present invention to provide the aforementioned method, wherein the polymer is methylcellulose, and the liquid medium contains 1 g/L or more of methylcellulose.

It is a further aspect of the present invention to provide the aforementioned method, wherein said L-amino acid is L-phenylalanine.

It is a further aspect of the present invention to provide a method for producing a lower alkyl ester of α-L-aspartyl-L-phenylalanine, comprising producing L-phenylalanine according to the aforementioned method and synthesizing the lower alkyl ester of α-L-aspartyl-L-phenylalanine from aspartic acid or its derivative and the L-phenylalanine.

It is a further aspect of the present invention to provide the aforementioned method, further comprising A) esterifying L-phenylalanine to generate a lower alkyl ester of L-phenylalanine, B) condensing the lower alkyl ester of L-phenylalanine with the N-acyl-L-aspartic anhydride, C) separating the lower alkyl ester of N-acyl-α-L-aspartyl-L-phenylalanine from the reaction mixture, and D) hydrogenating the lower alkyl ester of N-acyl-α-L-aspartyl-L-phenylalanine to generate the lower alkyl ester of α-L-aspartyl-L-phenylalanine.

DESCRIPTION OF THE PREFERRED EMBODIMENTS

An exemplary method of the present invention is to produce an L-amino acid by fermentation by culturing a microorganism which is able to produce an L-amino acid in a liquid medium so that the L-amino acid precipitates in the medium, wherein the medium contains a polymer such as a water-soluble cellulose derivative, a water-soluble polyvinyl compound, a polar organic solvent-soluble polyvinyl compound, a water-soluble starch derivative, an alginic acid salt, and a polyacrylic acid salt.

The term "L-amino acid" is not particularly limited so long as it is able to precipitate in a medium during fermentation using a microorganism. Specific examples include hydrophobic amino acids and acidic amino acids. Examples of the hydrophobic amino acids include L-valine, L-leucine, and L-isoleucine, which are branched chain amino acids, and L-tryptophan, L-phenylalanine and L-tyrosine, which are aromatic L-amino acids. Furthermore, examples of the acidic amino acids include L-glutamic acid. The L-amino acids also include L-threonine.

Examples of the water-soluble cellulose derivative include carboxymethylcellulose, methylcellulose, sodium carboxymethylcellulose, hydroxypropylcellulose, hydroxypropylcellulose phthalate, and so forth. Examples of the water-soluble polyvinyl compound or the polar organic solvent-soluble polyvinyl compound include polyvinylpyrrolidone, polyvinyl alcohol, polyvinylacetal diethylaminoacetate and so forth. Examples of the water-soluble starch derivative include hydroxypropyl starch, gelatin and so forth. Examples of the alginic acid salt include alginic acid alkali metal salts such as sodium arginate and so forth, and examples of polyacrylic acid salt include sodium polyacrylate and so forth.

These polymers may be independently added to the medium, or two or more of may be added to the medium in various combinations.

The concentration of the polymer in the medium is not particularly limited so long as it does not inhibit production and precipitation of the objective L-amino acid. A suitable polymer concentration can be appropriately determined depending on the chosen microorganism, objective L-amino acid, and the type of the polymer chosen. For example, a suitable concentration can be determined by adding the polymer to a medium at various concentrations and measuring the yield or production rate, and the amount of precipitated L-amino acid. Specifically, an example of the polymer concentration is 10 mg/L or more, another example is 1 g/L or more, and another example is 1.7 g/L or more. Although the upper limit of the concentration is not particularly limited so long as it does not inhibit production and precipitation of the objective L-amino acid, it can be, for example, 2 g/L.

The amount of the polymer in the medium can be measured by a method suitable for the specific type of polymer employed. For example, methylcellulose, etc., can be measured by the methoxyl assay. The methoxyl assay is performed by adding hydroiodic acid to a sample, heating the mixture, oxidizing the produced methyl iodide with bromine, and titrating the produced iodic acid with a sodium thiosulfate solution to quantify methoxyl groups (reference: http://www.tokyo-eiken.go.jp/additives/kijun-1.html).

The polymer may be added to the medium at any time so long as the objective L-amino acid is able to precipitate into the medium. The polymer may be added to the medium at the start of the culture, or it may be added in the middle of the culture. Moreover, the polymer may be added to the medium by fed-batch culture, which is described later.

Any medium may be used so long as it contains a carbon source, a nitrogen source, and the polymer as nutrients. A batch culture, fed-batch culture, and/or continuous culture may be used.

A fed-batch culture refers to a culture method in which the medium is continuously or intermittently fed into the culture vessel, and the medium is not extracted until the end of the culture. A continuous culture means a method in which the medium is continuously or intermittently fed into the culture vessel, and the medium is extracted from the vessel (usually in a volume equivalent to the volume of the fed medium) at the same time. The starting medium means the medium used in the batch culture before feeding the feed medium in the fed-batch culture or continuous culture. Feed medium means a medium which is supplied to the fermentation tank in the fed-batch culture or continuous culture. The feed medium may contain all or a part of the components necessary for the growth of a microorganism. The term "fermentation medium" means a medium contained in a fermenter, and an L-amino acid is collected from this fermentation medium. Furthermore, the term "fermenter" means a vessel in which the L-amino acid production is performed, and the shape of this vessel is not limited. A fermentation tank or a jar fermenter may be used. Furthermore, the volume of the fermenter is not limited so long as an L-amino acid can be produced and collected.

Although the polymer may be added at an early stage of the culture or in the middle of the culture as described above, for example, when the method includes a proliferation stage of the microorganism (proliferation phase) and a production stage (L-amino acid production phase), the polymer is preferably present at a certain concentration during at least the L-amino acid production phase.

The "proliferation phase" means the stage when the carbon source is primarily used for cell growth, that is, the stage when the microorganism is logarithmically proliferating, within 3 hours, preferably 6 hours, more preferably 10 hours, from the start of the culture. The "L-amino acid production phase" means the stage when the carbon source is mainly used for L-amino acid production after a period of 3 hours, preferably 6 hours, more preferably 10 hours, from the start of the culture.

As the carbon source in the medium, saccharides such as glucose, glycerol, fructose, sucrose, maltose, mannose, galactose, starch hydrolysate, and molasses can be used, and glucose and sucrose are particularly preferred. In addition, organic acids such as acetic acid and citric acid and alcohols such as ethanol can also be used alone or in combination with another carbon source. Furthermore, as a raw material of the carbon source, cane molasses, beet molasses, high test molasses, and citrus molasses may be used, and hydrolysates of natural raw materials such as cellulose, starch, corn, cereal, and tapioca may also be used. Furthermore, carbon dioxide dissolved in the culture medium can also be used as the carbon source. These carbon sources can be used in the starting medium and feed medium. The medium may contain one or two or more kinds of these carbon sources. Furthermore, the same carbon source may be used for the starting medium and the feed medium, or the carbon source of the feed medium may be different from that of the starting medium. For example, glucose may be used as the carbon source of the starting medium, while sucrose may be used as the carbon source of the feed medium.

As the nitrogen source in the medium, ammonia, ammonium salts such as ammonium sulfate, ammonium carbonate, ammonium chloride, ammonium phosphate, ammonium acetate, urea, nitrates, and so forth can be used. Ammonia gas and aqueous ammonia used to adjust the pH can also be utilized as the nitrogen source. Furthermore, peptone, yeast extract, meat extract, malt extract, corn steep liquor, soybean hydrolysate, and so forth can also be utilized. The medium may contain one or more of these nitrogen sources. These nitrogen sources can also be used for both the starting medium and the feed medium. Furthermore, the same nitrogen source can be used for both the starting medium and the feed medium, or the nitrogen source of the feed medium may be different from that of the starting medium.

The medium may contain a phosphoric acid source in addition to the carbon source and the nitrogen source. As the phosphoric acid source, potassium dihydrogenphosphate, dipotassium hydrogenphosphate, phosphate polymers such as pyrophosphoric acid, and so forth can be utilized.

Furthermore, the medium may contain a growth promoting factor, such as a nutrient with a growth promoting effect, in addition to the carbon source and nitrogen source. As the growth promoting factor, trace metals, amino acids, vitamins, fatty acids, nucleic acids as well as peptone, casamino acid, yeast extract, soybean protein degradation product, and so forth containing the foregoing substances can be used. Aromatic amino acids and branched chain amino acids, in particular, share a common biosynthesis system, and therefore a biosynthesis system of the microorganism for an amino acid other than the objective amino acid may be attenuated as described later. In such a case, it is preferable to add the amino acid for which biosynthesis system is attenuated to the medium. For example, when the objective amino acid is L-tryptophan, it is desirable to add L-phenylalanine and/or tyrosine, and when the object amino acid is L-phenylalanine, it is desirable to add L-tryptophan and/or L-tyrosine (WO2003/048374).

Examples of the trace metals include iron, manganese, magnesium, calcium, and so forth. Examples of the vitamins include vitamin $B_1$, vitamin $B_2$, vitamin $B_6$, nicotinic acid, nicotinamide, vitamin $B_{12}$, pyridoxine, and so forth. These growth promoting factors may be present in the starting medium or the feed medium.

Furthermore, when an auxotrophic mutant that requires an amino acid or the like for growth is used, it is preferable to supplement the required nutrient to the medium. In particular, since the L-lysine biosynthetic pathway is enhanced and L-lysine degrading ability is often attenuated in an L-amino acid-producing bacteria, one or more of L-lysine, L-homoserine, L-isoleucine, and L-methionine can be added.

The starting medium and the feed medium may have the same or different compositions. When both the starting medium and the feed medium include the polymer, concentrations of the polymer may be the same or different. Furthermore, when the feed medium is fed at multiple stages, the compositions of the feed media fed at the various stages may be the same or different.

The culture is preferably performed as an aeration culture at a fermentation temperature of 20 to 45° C., particularly preferably at 30 to 42° C. The oxygen concentration is adjusted to 5 to 50%, desirably about 10%. Furthermore, the aeration culture is preferably performed with the pH adjusted to 5 to 9. If pH is lowered during the culture, for example, calcium carbonate or an alkali such as ammonia gas and aqueous ammonia is added to neutralize the culture. When the objective amino acid is an acidic amino acid, for example, L-glutamic acid, it is desirable to perform the culture at pH 3 to 9, preferably pH 3 to 5. When the culture is performed under such conditions preferably for about 10 to 120 hours, a marked amount of L-amino acid is produced in the culture medium. Although the concentration of L-amino acid which accumulates is not limited so long as it is higher than that observed with wild-type strains and the L-amino acid can be isolated and collected from the medium, one example is 50 g/L or higher, another example is 75 g/L or higher, and another example is 100 g/L or higher. Although the L-amino acid may dissolve or precipitate in the medium, it is preferred that at least a part of it precipitates into the medium.

The L-amino acid can be collected by a known collection method from the culture medium after the culture. For example, the L-amino acid precipitated in the medium can be collected by centrifugation or filtration. Moreover, when the L-amino acid precipitates into the medium, the L-amino acid which is dissolved in the medium may be crystallized, and then the precipitated L-amino acid and the crystals may be isolated together.

The culture of the microorganism may be performed as a seed culture and a main culture in order to ensure accumulation of more L-amino acid than a certain level. The seed culture may be performed as a shaking culture using a flask or the like, or batch culture, and the main culture may be performed as a fed-batch culture or a continuous culture. Alternatively, both the seed culture and the main culture may be performed as batch culture.

In these culture methods, when the L-amino acid concentration reaches the intended level, a part of the L-amino acid may be extracted, and fresh medium may be added to repeat the culture. As the fresh medium to be added, a medium containing a carbon source and a nutrient having a growth promoting effect (growth promoting factor) is preferred. As the carbon source, glucose, sucrose, fructose, and glycerol are preferred. As the growth promoting factor, nitrogen sources, phosphoric acid, amino acids, and so forth are preferred. As the nitrogen source, ammonia, ammonium salts such as ammonium sulfate, ammonium carbonate, ammonium chloride, ammonium phosphate, ammonium acetate, urea, nitrates, and so forth can be used. Furthermore, as the phosphoric acid source, potassium dihydrogenphosphate and dipotassium hydrogenphosphate can be used. As for the amino acids, when an auxotrophic mutant strain is used, it is preferable to supplement with the required nutrient.

When a fed-batch culture or a continuous culture is performed, the feed medium may be intermittently fed so that the supply of saccharide or nutrition source is temporarily stopped. The supply of the feed medium is stopped, for example, at maximum, 30% or less, 20% or less, or 10% or less, of the feeding time. When the feed medium is intermittently fed, the feed medium may be initially added over a predetermined time, and the second and following additions may be controlled to begin when a rise in the pH or dissolved oxygen concentration is detected by a computer upon depletion of the carbon source in the fermentation medium during the addition-stopped period prior to a certain medium-addition period, and thus the substrate concentration in the culture tank is always automatically maintained at a low level (U.S. Pat. No. 5,912,113).

As the carbon source, glucose, sucrose, and fructose are preferred. As the growth promoting factor, nitrogen sources, phosphoric acid, amino acids, and so forth are preferred. As the nitrogen source, ammonia, ammonium salts such as ammonium sulfate, ammonium carbonate, ammonium chloride, ammonium phosphate, ammonium acetate, urea, nitrates, and so forth can be used. Furthermore, as the phosphoric acid source, potassium dihydrogenphosphate and dipotassium hydrogenphosphate can be used. As for the amino acids, when an auxotrophic mutant strain is used, it is preferable to supplement with the required nutrient. Furthermore, the feed medium may be one type of medium, or a mixture of two or more types of media. When two or more types of feed media are used, the media may be mixed and fed by using one feed can, or the media may be separately fed by using two or more feed cans.

When a fed-batch culture is performed, the feed medium is preferably fed in such an amount that the saccharide amount in the feed medium or the whole fermentation medium does not exceed 30 g/L, and it can be controlled to be 20 g/L or lower, or 10 g/L or lower. In particular, the saccharide concentration can be controlled so that it is in the aforementioned concentration range especially at the end of the logarithmic proliferation of the microorganism. The feed rate of the carbon source can be controlled by using the method described in U.S. Pat. No. 5,912,113. Furthermore, saccharide and phosphoric acid can be fed at such concentrations so that saccharide and phosphoric acid serve as limiting factors of the bacterial cell growth. Phosphoric acid can be present in the feed medium in an amount of 2 or lower, for example, or 1.5 or lower, or even 1 or lower, expressed in terms of the phosphorous/carbon (P/C) ratio (refer to U.S. Pat. No. 5,763,230).

When the continuous culture method is used, the medium may be extracted and fed simultaneously, or a part of the medium may be extracted, and then the medium may be fed. Furthermore, the method may also be a continuous culture method including recycling cells in which the culture medium containing L-amino acid and bacterial cells is extracted, and only the cells are returned to the fermenter (French Patent No. 2669935). As the method for continuously or intermittently feeding a nutrient source, the same method as used in the fed-batch culture is used.

When the culture medium is intermittently extracted, a part of the L-amino acid can be extracted when the L-amino acid concentration reaches a predetermined level, and a fresh medium can be fed to continue the culture. Furthermore, the culture can be performed so that the final volume of the medium after adding the medium is equal to the volume of the culture medium before the extraction. The term "equal" means that the volume after the addition of the medium corresponds to about 93 to 107% of the volume of the medium before the extraction.

When the culture medium is continuously extracted, the extraction can be started at the same time as or after the feeding of the nutrient medium. For example, within 5 hours, or 3 hours, or even 1 hour, after the start of the feeding, the extraction can be started. Furthermore, the extraction volume of the culture medium can be equal to the volume of the fed medium.

The continuous culture method of recycling bacterial cells includes intermittently or continuously extracting the fermentation medium when the amino acid concentration reaches a predetermined level, extracting only L-amino acid, and re-circulating filtration residues containing bacterial cells into the fermenter, and it can be performed by referring to, for example, French Patent No. 2669935.

Phenylalanine produced by the method may be used, for example, to produce a lower alkyl ester of α-L-aspartyl-L-phenylalanine (also referred to as "aspartame"). That is, an exemplary method of the present invention includes a method for producing a lower alkyl ester of α-L-aspartyl-L-phenylalanine by using L-phenylalanine as a raw material. The method includes synthesizing a lower alkyl ester of α-L-aspartyl-L-phenylalanine from the L-phenylalanine which is produced by the aforementioned method, and aspartic acid or its derivative. Examples of the lower alkyl ester include methyl ester, ethyl ester, propyl ester, and so forth.

The method for synthesizing a lower alkyl ester of α-L-aspartyl-L-phenylalanine from L-phenylalanine and aspartic acid or its derivative is not particularly limited, and any conventional method can be employed so long as L-phenylalanine or its derivative can be used for synthesis of a lower alkyl ester of α-L-aspartyl-L-phenylalanine. For example, a lower alkyl ester of α-L-aspartyl-L-phenylalanine may be produced by the following method (U.S. Pat. No. 3,786,039). L-Phenylalanine is esterified to obtain a lower alkyl ester of L-phenylalanine. The L-phenylalanine alkyl ester is reacted with an L-aspartic acid derivative with a protected β-carboxyl group and an α-carboxyl group is esterified for activation. Examples of such a derivative include N-acyl-L-aspartic anhydride such as N-formyl-, N-carbobenzoxy-, or N-p-methoxycarbobenzoxy-L-aspartic anhydride. By this condensation reaction, a mixture of N-acyl-α-L-aspartyl-L-phenylalanine and N-acyl-β-L-aspartyl-L-phenylalanine is obtained. If the condensation reaction is performed in the presence of an organic acid with an acid dissociation constant at 37° C. of $10^{-4}$ or less, the ratio of the α-isomer to the β-isomer in the mixture is increased (Japanese Patent Laid-Open No. 51-113841). Then, the N-acyl-α-L-aspartyl-L-phenylalanine is separated from the mixture, followed by hydrogenation to obtain α-L-aspartyl-L-phenylalanine.

The chosen microorganism is able to produce an L-amino acid and can cause accumulation of the L-amino acid by precipitation of the L-amino acid in a liquid medium when it is cultured in the medium.

The solubilities of the amino acids at 20° C. are as shown in Table 1, and strains which can produce an amino acid in an amount of 10.6 g/L or more in the case of L-tryptophan fermentation, 27.4 g/L or more in the case of L-phenylalanine fermentation, 0.38 g/L in the case of L-tyrosine fermentation, 41.2 g/L or more in the case of L-isoleucine fermentation, 23.8 g/L or more in the case of L-leucine fermentation, 57.5 g/L or more in the case of L-valine fermentation, 7.2 g/L in the case of L-glutamic acid fermentation, or 90.0 g/L or more in the case of L-threonine fermentation can be used.

TABLE 1

| L-Amino acid | Solubility (20° C.) g/L | Solubility (40° C.) g/L |
| --- | --- | --- |
| L-Tryptophan | 10.6 | 14 |
| L-Phenylalanine | 27.4 | 38 |
| L-Tyrosine | 0.38 | 0.75 |
| L-Isoleucine | 41.2 | 44 |
| L-Leucine | 23.8 | 26 |

TABLE 1-continued

| L-Amino acid | Solubility (20° C.) g/L | Solubility (40° C.) g/L |
| --- | --- | --- |
| L-Valine | 57.5 | 65 |
| L-Glutamic acid | 7.2 | 15 |
| L-Threonine | 90.0 | 122 |

When the pH of an aqueous solution containing L-glutamic acid is reduced, the solubility of L-glutamic acid markedly decreases around pKa (4.25) of the 7-carboxyl group, and is the lowest at the isoelectric point (pH 3.2). Although it also depends on the medium composition, L-glutamic acid usually dissolves at 10 to 20 g/L at pH 3.2, 30 to 40 g/L at pH 4.0, and 50 to 60 g/L at pH 4.7, at about 30° C.

As the chosen microorganism or a parent strain which can be used to derive the microorganism, microorganisms belonging to the family Enterobacteriaceae, typical examples of which are *Escherichia* bacteria and *Pantoea* bacteria, coryneform bacteria, and so forth can be used. In addition, methanol-utilizing bacteria such as *Methylophilus* bacteria and *Methylobacillus* bacteria, which can produce L-amino acid from methanol, may also be used. Further examples of microorganisms belonging to the family Enterobacteriaceae include enterobacteria belonging to γ-proteobacteria such as those belonging to the genus *Enterobacter, Klebsiella, Serratia, Erwinia, Salmonella, Morganella*, or the like, and examples of other microorganisms include *Alicyclobacillus* bacteria, *Bacillus* bacteria, yeasts belonging to the genus *Saccharomyces, Candida*, or the like and so forth.

As the *Escherichia* bacteria, those mentioned in the work of Neidhardt et al. (Neidhardt, F. C. et al., *Escherichia coli and Salmonella Typhimurium*, American Society for Microbiology, Washington D.C., 1208, table 1), such as *Escherichia coli*, can be utilized. Examples of wild-type strains of *Escherichia coli* include, for example, the K12 strain and derivatives thereof, *Escherichia coli* MG1655 strain (ATCC No. 47076), W3110 strain (ATCC No. 27325), and so forth. They are available from the American Type Culture Collection (ATCC, Address: P.O. Box 1549, Manassas, Va. 20108, United States of America).

Furthermore, examples of the *Enterobacter* bacteria include *Enterobacter agglomerans*, *Enterobacter aerogenes* and so forth, and examples of the *Pantoea* bacteria include *Pantoea ananatis*. Some species of *Enterobacter agglomerans* have been recently re-classified into *Pantoea agglomerans*, *Pantoea ananatis*, *Pantoea stewartii* or the like, based on the nucleotide sequence analysis of 16S rRNA, etc. Both of the *Enterobacter* bacteria and *Pantoea* bacteria may be used so long as the chosen bacterium is classified into the family Enterobacteriaceae. When a *Pantoea ananatis* strain is bred by a genetic engineering technique, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

Specific examples of the *Methylophilus* bacteria include *Methylophilus methylotrophus*, and typical examples of *Methylophilus methylotrophus* include the AS1 strain (NCIMB 10515) and so forth. The *Methylophilus methylotrophus* AS1 strain is available from the National Collections of Industrial and Marine Bacteria (Address: NCIMB Lts., Torry Research Station, 135, Abbey Road, Aberdeen AB9 8DG, United Kingdom).

Specific examples of the *Methylobacillus* bacteria include *Methylobacillus glycogenes, Methylobacillus flagellatum*, and so forth. Examples of *Methylobacillus glycogenes* include the T-11 strain (NCIMB 11375), ATCC 21276 strain, ATCC 21371 strain, ATR80 strain (described in Appl. Microbiol. Biotechnol., vol. 42, pp. 67-72, 1994), A513 strain (described in Appl. Microbiol. Biotechnol., vol. 42, pp. 67-72 (1994)), and so forth. The *Methylobacillus glycogenes* NCIMB 11375 strain can be obtained from the National Collections of Industrial and Marine Bacteria (Address: NCIMB Lts., Torry Research Station 135, Abbey Road, Aberdeen AB9 8DG, United Kingdom). Examples of *Methylobacillus flagellatum* include the KT strain (described in Arch. Microbiol., vol. 149, pp. 441-446, 1988) and so forth.

The coryneform bacteria are a group of microorganisms defined in Bergey's Manual of Determinative Bacteriology, 8th Ed., p. 599 (1974), and microorganisms classified into such aerobic, Gram-positive and nonacid-fast bacilli which are unable to sporulate can be used. The coryneform bacteria include bacteria which have previously been classified into the genus *Brevibacterium* but are presently united into the genus *Corynebacterium* (Int. J. Syst. Bacteriol. 41:255-260 (1991)), and bacteria belonging to the genus *Brevibacterium* or *Microbacterium*, which are closely related to the genus *Corynebacterium*.

Specific examples of such coryneform bacteria include the following:
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specific examples of these bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium efficiens* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869 (*Corynebacterium glutamicum* TCC 13869)
*Brevibacterium roseum* ATCC 13825

*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

These strains are available from, for example, the American Type Culture Collection (ATCC) (Address: P.O. Box 1549, Manassas, Va. 2010812301 United States of America). That is, each strain is given a unique registration number which is listed in the catalogue of the ATCC (http://www.atcc.org/). Strains can be ordered by using this registration number. The AJ12340 strain was deposited on Oct. 27, 1987 in National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-5466, Japan), with a deposit number of FERM BP-1539 under the provisions of Budapest Treaty. The AJ12418 strain was deposited on Jan. 5, 1989 in National Institute of Bioscience and Human Technology of Agency of Industrial Science and Technology, with a deposit number of FERM BP-2205 under the provisions of the Budapest Treaty.

Hereinafter, methods for imparting an L-amino acid-producing ability to such bacteria as mentioned above are described.

To impart the ability to produce an L-amino acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include acquiring an auxotrophic mutant, an analogue-resistant strain, or a metabolic regulation mutant, constructing a recombinant strain so that it overexpresses an L-amino acid biosynthesis enzyme, and so forth. Here, in the breeding of an L-amino acid-producing bacteria, one or more of the above described properties such as auxotrophy, analogue resistance, and metabolism regulation mutation may be imparted. Expression of one or two or more of the L-amino acid biosynthesis enzymes can be enhanced. Furthermore, the methods of imparting properties such as auxotrophy, analogue resistance, or metabolic regulation mutation may be combined with enhancement of the biosynthesis enzymes.

An auxotrophic mutant strain, L-amino acid analogue-resistant strain, or metabolic regulation mutant strain with an ability to produce an L-amino acid can be obtained by subjecting a parent strain or wild-type strain to a conventional mutagenesis, such as exposure to X-rays or UV irradiation, or treatment with a mutagen such as N-methyl-N'-nitro-N-nitrosoguanidine, etc., and then selecting those which exhibit an autotrophy, analogue resistance, or metabolic regulation mutation and which also have the ability to produce an L-amino acid.

Methods for imparting amino acid-producing ability and amino acid-producing bacteria will be specifically exemplified below.

L-tryptophan, L-phenylalanine, and L-tyrosine are all aromatic amino acids and share a common biosynthesis pathway. Examples of the genes encoding the biosynthesis enzymes for these aromatic amino acids include deoxyarabino-heptulosonate phosphate synthase (aroG), chorismate mutase-prephenate dehydratase (pheA), 3-dehydroquinate synthase (aroB), shikimic acid dehydrogenase (aroE), shikimate kinase (aroL), 5-enolpyruvylshikimate-3-phosphate synthase (aroA), and chorismate synthase (aroC) (EP763127). It is known that these genes are controlled by the tyrosine repressor (tyrR), so activity of an aromatic amino acid biosynthesis enzyme may also be increased by deleting the tyrR gene (see EP763127). The abbreviations in parentheses after the enzyme names represent the gene names (the same shall apply to the same occasions hereafter).

In order to enhance an aromatic amino acid productivity of a bacterium, biosynthesis of an amino acid other than the target aromatic amino acid may be attenuated. For example, when the target amino acid is L-tryptophan, biosynthetic pathways of L-phenylalanine and/or L-tyrosine may be attenuated (U.S. Pat. No. 4,371,614).

Furthermore, 3-deoxy-D-arabinoheptulosonate-7-phosphate synthetase (aroF, aroD) is subjected to feedback inhibition by aromatic amino acids. Therefore, the enzyme may be modified so that it is not subject to the feedback inhibition. An aromatic L-amino acid-producing bacterium can be obtained by, for example, introducing a mutant aroF in which the L-aspartic acid at position 147 or the L-serine at position 181 is replaced by another amino acid, or introducing a mutant aroD gene in which the L-aspartic acid at position 146, the L-methionine at position 147, either the L-proline at position 150 or the L-alanine at position 202, or both the L-methionine at position 157 and the L-alanine at position 219 are replaced by other amino acid(s) (EP0488424). Furthermore, chorismate mutase-prephenate dehydratase also is subject to feedback inhibition by an aromatic amino acid, and therefore they may be modified so as not to be subject to the feedback inhibition.

An example of a gene involved in the synthesis of branched chain amino acids includes the ilvGMEDA operon, and this operon is subject to expression control (attenuation) by L-valine and/or L-isoleucine and/or L-leucine. Therefore, productivity of a microorganism for these L-amino acids can be improved by introducing into the microorganism the ilvGMEDA operon in which the region required for attenuation is removed.

Aromatic amino acids and branched chain amino acids share a common biosynthesis system, and therefore it is preferable to use a strain in which a biosynthesis system for an aromatic amino acid or branched chain amino acid other than the objective L-amino acid is attenuated. For example, a strain which can efficiently produce an objective L-amino acid can be obtained by attenuating the biosynthesis system of L-phenylalanine and L-tyrosine when the objective amino acid is L-tryptophan, attenuating the biosynthesis system of L-tryptophan and L-tyrosine when the objective amino acid is L-phenylalanine, attenuating the biosynthesis system of L-leucine and L-isoleucine when the objective amino acid is L-valine, attenuating the biosynthesis system of L-valine and L-leucine when the objective amino acid is L-isoleucine, or attenuating the biosynthesis system of L-valine and L-isoleucine when the objective amino acid is L-leucine. Attenuation of a biosynthesis system can be attained by introducing a mutation into a gene coding for an enzyme of the biosynthesis system or obtaining a strain which requires an L-amino acid synthesized by a biosynthesis system desired to be attenuated using a synthetic medium containing that L-amino acid.

Methods for imparting L-amino acid-producing ability and microorganisms to which L-amino acid-producing ability is imparted are exemplified below.

L-Tryptophan-Producing Bacteria

Examples of L-tryptophan-producing bacteria and parent strains which can be used to derive them include, but are not limited to, strains belonging to the genus *Escherichia*, such as *E. coli* JP4735/pMU3028 (DSM10122) and JP6015/pMU91 (DSM10123) which is deficient in tryptophanyl-tRNA synthetase encoded by mutant trpS gene (U.S. Pat. No. 5,756, 345), *E. coli* AGX17 (pGX44) (NRRLB-12263) and AGX6 (pGX50)aroP (NRRLB-12264) deficient in the enzyme tryptophanase (U.S. Pat. No. 4,371,614), *E. coli* AGX17/ pGX50, pACKG4-pps in which a phosphoenolpyruvate-producing ability is enhanced (WO9708333, U.S. Pat. No. 6,319, 696), and the like. L-Tryptophan-producing bacteria belonging to the genus *Escherichia* which have enhanced activity of the protein encoded by the yedA or yddG gene may also be used (U.S. patent applications 2003/0148473 A1 and 2003/0157667 A1).

Examples of L-tryptophan-producing bacteria and parent strains which can be used to derive them also include strains in which one or more activities of the following enzymes are enhanced: anthranilate synthase (trpE), phosphoglycerate dehydrogenase (serA), and tryptophan synthase (trpAB). The anthranilate synthase and phosphoglycerate dehydrogenase are both subject to feedback inhibition by L-tryptophan and L-serine, therefore a mutation desensitizing the feedback inhibition may be introduced into these enzymes. Specific examples of strains having such a mutation include *E. coli* SV164 which harbors desensitized anthranilate synthase and a transformant strain SV164(pGH5) obtained by introducing into the *E. coli* SV164 the plasmid pGH5, which contains a mutant serA gene encoding a feedback inhibition-desensitized phosphoglycerate dehydrogenase.

The aforementioned *E. coli* SV164(trpE8) is a strain obtained by introducing a mutant trpE gene coding for anthranilate synthase which is desensitized to feedback inhibition into a trpE deficient strain, *Escherichia coli* KB862 (DSM7196) (WO94/08031, Japanese Patent Laid-open No. 7-507693). The *E. coli* SV164(pGH5) strain is obtained by introducing a plasmid pGH5 (WO94/08031) containing a mutant serA5 gene coding for phosphoglycerate dehydrogenase desensitized to feedback inhibition by serine into the SV164 strain. The SV164(pGH5) strain produces not only L-tryptophan but also L-serine (U.S. Pat. No. 7,045,320).

The aforementioned *E. coli* KB862 strain was designated AJ13828 and was deposited on Dec. 21, 2000 in the National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) as an international deposit under the provisions of the Budapest Treaty with a deposit number of FERM BP-7405.

Examples of L-tryptophan-producing bacteria and parent strains which can be used to derive them also include a strain which has enhanced activity of 3-phosphoserine phosphatase (serB) (U.S. Pat. No. 4,371,614), a strain which has enhanced activity of phosphoenolpyruvate carboxykinase (pck4) (WO2004/090125), and a strain which constitutively expresses the maleate synthase-isocitrate lyase-isocitrate dehydrogenase-kinase/phosphatase operon (ace operon) or in which expression of this operon is enhanced (WO2005/ 103275).

Examples of L-tryptophan-producing bacteria and parent strains for deriving them also include strains which have been transformed with the tryptophan operon containing a gene encoding inhibition-desensitized anthranilate synthase (Japanese Patent Laid-open Nos. 57-71397, 62-244382, U.S. Pat. No. 4,371,614). Moreover, L-tryptophan-producing ability may be imparted by enhancing expression of a gene which encodes tryptophan synthase in the tryptophan operon (trpBA). Tryptophan synthase consists of α and β subunits which are encoded by the trpA and trpB genes, respectively.

In addition, L-tryptophan-producing ability may be improved by enhancing expression of the isocitrate lyase-malate synthase operon (WO2005/103275).

*Corynebacterium glutamicum* AJ12118 (FERM BP-478, Japanese Patent No. 01681002), which is resistant to sulfaguanidine, the coryneform bacterium introduced with the tryptophan operon (Japanese Patent Laid-open No. 63-240794), and the coryneform bacterium introduced with a gene coding for shikimate kinase derived from a coryneform bacterium (Japanese Patent Laid-open No. 01-994749) can be used.

L-Phenylalanine-Producing Bacteria

Examples of L-phenylalanine-producing bacteria and parent strains which can be used to derive them include, but are not limited to, strains belonging to the genus *Escherichia*, such as *E. coli* AJ12479 (FERM BP-4796) (EP1484410A, see Embodiment 2), *E. coli* AJ12739 (tyrA::Tn10, tyrR) (VKPM B-8197), *E. coli* HW1089 (ATCC 55371) harboring a mutant pheA34 gene (U.S. Pat. No. 5,354,672), *E. coli* MWEC101-b (KR8903681), *E. coli* NRRLB-12141, NRRLB-12145, NRRLB-12146, and NRRLB-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) may be used (EP 488-424 B1). Furthermore, L-phenylalanine-producing bacteria belonging to the genus *Escherichia* with an enhanced activity of the protein encoded by the yedA gene or the yddG gene may also be used (U.S. Patent Applications 2003/0148473 A1 and 2003/0157667 A1).

As phenylalanine-producing coryneform bacteria, the *Cornebacterium glutamicum* BPS-13 (FERM BP-1777), K77 (FERM BP-2062), and K78 (FERM BP-2063) (European Patent Laid-open No. 331145, Japanese Patent Laid-open No. 02-303495), of which phosphoenolpyruvate carboxylase or pyruvate kinase activity is reduced, tyrosine-auxotrophic strain (Japanese Patent Laid-open No. 05-049489), and so forth can be used.

Phenylalanine-producing bacteria which have been modified to incorporate by-products, for example, by increasing the expression of the L-tryptophan uptake gene, tnaB or mtr, or the L-tyrosine uptake gene, tyrP, can also be obtained (EP1484410).

L-Tyrosine-Producing Bacteria

Examples of tyrosine-producing bacteria include *Escherichia* bacteria with a desensitized prephenate dehydratase gene (tyrA). The expression product of this gene is desensitized to inhibition by tyrosine (European Patent Application Laid-open No. 1616940).

L-Valine-Producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). The region in the ilvGMEDA operon which is required for attenuation can be removed so that expression of the operon is not attenuated by the L-valine that is produced. Furthermore, it is preferred that the ilvA gene in the operon is disrupted so that threonine deaminase activity is decreased.

Examples of L-valine-producing bacteria which can be used to derive L-valine-producing bacteria also include mutant strains with amino-acyl t-RNA synthetase having a mutation (U.S. Pat. No. 5,658,766). For example, *E. coli* VL1970, which has a mutation in the ileS gene encoding isoleucine tRNA synthetase, can be used. *E. coli* VL1970 was deposited at the Russian National Collection of Industrial Microorganisms (VKPM) (1 Dorozhny proezd., 1 Moscow 117545, Russia) on Jun. 24, 1988 under an accession number VKPM B-4411.

Furthermore, mutants requiring lipoic acid for growth and/or lacking H$^+$-ATPase can also be used as parent strains (WO96/06926).

Examples of L-valine-producing bacteria of coryneform bacteria include, for example, strains modified so that expression of a gene encoding an L-valine biosynthetic enzyme is enhanced. Examples of the L-valine biosynthesis enzyme include enzymes encoded by genes present on the ilvBNC operon, that is, acetohydroxy acid synthetase encoded by ilvBN and isomero-reductase encoded by ilvC (WO00/50624). Since the ilvBNC operon is subject to transcription regulation by L-valine and/or L-isoleucine and/or L-leucine, it is desirable to eliminate attenuation to avoid transcriptional suppression by L-valine that is produced.

Impartation of L-valine-producing ability to coryneform bacteria may be performed by decreasing or eliminating activity of at least one kind of enzyme which is involved in a metabolic pathway that decreases L-valine production. For example, reduction of the activity of threonine dehydratase involved in the L-leucine synthesis, or activity of an enzyme that involved in D-panthothenate synthesis is contemplated (WO00/50624).

L-Valine-producing ability may also be imparted by imparting resistance to an amino acid analogue or the like.

Examples include, for example, mutant strains which are auxotrophic for L-isoleucine and L-methionine, and resistant to D-ribose, purine ribonucleoside or pyrimidine ribonucleoside (FERM P-1841, FERM P-29, Japanese Patent Publication No. 53-025034), mutant strains resistant to polyketides (FERM P-1763, FERM P-1764, Japanese Patent Publication No. 06-065314), and mutant strains resistant to L-valine in a medium containing acetic acid as the sole carbon source and sensitive to pyruvic acid analogues such as fluoropyruvic acid in a medium containing glucose as the sole carbon source (FERM BP-3006, BP-3007, Japanese Patent No. 3006929).

L-Isoleucine-Producing Bacteria

Examples of L-isoleucine-producing bacteria and parent strains which can be used to derive L-isoleucine-producing bacteria include, but are not limited to, mutants having resistance to 6-dimethylaminopurine (Japanese Patent Laid-open No. 5-304969), mutants having resistance to an isoleucine analogue such as thiaisoleucine and isoleucine hydroxamate, and mutants additionally having resistance to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxy acid synthase, can also be used as parent strains (Japanese Patent Laid-open No. 2-458, FR 0356739, and U.S. Pat. No. 5,998,178).

Examples of L-isoleucine-producing strains of coryneform bacteria include the coryneform bacterium of which brnE gene coding for a branched chain amino acid secretion protein is amplified (Japanese Patent Laid-open No. 2001-169788), the coryneform bacterium imparted with L-isoleucine-producing ability by protoplast fusion with an L-lysine-producing bacterium (Japanese Patent Laid-open No. 62-74293), the coryneform bacterium of which homoserine dehydrogenase is enhanced (Japanese Patent Laid-open No. 62-91193), the threonine hydroxamete-resistant strain (Japanese Patent Laid-open No 62-195293), α-ketomalonic acid resistant strain (Japanese Patent Laid-open No. 61-15695), and the methyl lysine resistant strain (Japanese Patent Laid-open No. 61-15696).

L-Leucine-Producing Bacteria

Examples of L-leucine-producing bacteria and parent strains for deriving L-leucine-producing bacteria include, but are not limited to, *Escherichia* bacteria, such as *E. coli* strains resistant to leucine (for example, the strain 57 (VKPM B-7386, U.S. Pat. No. 6,124,121)) or leucine analogues including β-2-thienylalanine, 3-hydroxyleucine, 4-azaleucine and 5,5,5-trifluoroleucine (Japanese Patent Publication No. 62-34397 and Japanese Patent Laid-open No. 8-70879); *E. coli* strains obtained by the genetic engineering method described in WO96/06926; and *E. coli* H-9068 (Japanese Patent Laid-open No. 8-70879).

The bacterium may also be improved by enhancing the expression of one or more genes involved in L-leucine biosynthesis. Examples of such genes include genes of the leuABCD operon, which are preferably represented by a mutant leuA gene coding for isopropylmalate synthase desensitized to feedback inhibition by L-leucine (U.S. Pat. No. 6,403,342). In addition, the may be improved by enhancing the expression of one or more genes coding for proteins which excrete L-amino acid from the bacterial cell. Examples of such genes include the b2682 and b2683 genes (ygaZH genes) (EP 1239041 A2).

Examples of L-leucine-producing strains of coryneform bacteria include the 2-thiazolealanine and β-hydroxyleucine-resistant strains (Japanese Patent Laid-open No. 8-266295), the valine analogue-resistant strain (Japanese Patent Laid-open No. 63-248392), the valine auxotrophic strain (Japanese Patent Publication No. 38-4395), the S-(2-aminoethyl)-L-cysteine (AEC) resistant strain (Japanese Patent Publication No. 51-37347), and the phenylalanine, valine and isoleucine auxotrophic strain (Japanese Patent Publication No. 54-36233).

L-Glutamic Acid-Producing Bacteria

Preferred examples of L-glutamic acid-producing bacteria include strains in which expression of one or more genes encoding an L-glutamic acid biosynthetic enzyme is enhanced. Examples of such genes include, but are not limited to, genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pjkA, pjkB), glucose phosphate isomerase (pgi), and so forth.

Examples of strains which have been modified so that expression of the citrate synthetase gene, the phosphoenolpyruvate carboxylase gene, the isocitrate dehydrogenase gene, the pyruvate dehydrogenase gene, and/or the glutamate dehydrogenase gene is enhanced include those disclosed in EP 1078989 A, EP 955368 A, and EP 952221A.

The modification for imparting L-glutamic acid producing ability may be attained by reducing or eliminating the activity of an enzyme that catalyzes a reaction branching off from the L-glutamic acid biosynthesis pathway and producing a compound other than L-glutamic acid. Examples of such an enzyme include isocitrate lyase, α-ketoglutarate dehydrogenase, acetohydroxy acid synthase, acetolactate synthase, formate acetyltransferase, lactate dehydrogenase, glutamate decarboxylase, 1-pyrroline-5-carboxilate dehydrogenase, and so forth.

For example, in order to reduce the α-ketoglutarate dehydrogenase activity, a modification may be performed by using the sucA (odhA) gene coding for the E1o subunit of the enzyme. Examples of strains with reduced α-ketoglutarate dehydrogenase activity include, for example, the following strains:

*Brevibacterium lactofermentum* ΔS strain (WO95/34672)
*Brevibacterium lactofermentum* AJ12821 (FERM BP-4172; FR9401748)
*Brevibacterium flavum* AJ12822 (FERM BP-4173; FR9401748)
*Corynebacterium glutamicum* (FERM BP-4174; FR9401748)
*Pantoea ananatis* AJ13601 (FERM BP-7207)
*Klebsiella planticola* AJ13410 (FERM BP-6617)
*Pantoea ananatis* AJ13355 (FERM BP-6614)

*Pantoea ananatis* AJ13356 is deficient in α-ketoglutarate dehydrogenase activity as a result of disruption of the αKGDH-E1 subunit gene (sucA). This strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, it is described as *Pantoea ananatis* in this specification.

Furthermore, the ability to produce L-glutamic acid in coryneform bacteria can also be achieved by amplifying the yggB gene (NCgl 1221; NP_600492. Reports small-conductance. [gi: 19552490], WO2006/070944), and introducing a mutant yggB gene in which a mutation is introduced into the coding region.

Examples of other methods for imparting or enhancing L-glutamic acid-producing ability include by imparting resistance to an organic acid analogue, a respiratory chain inhibitor, etc., and by imparting sensitivity to a cell wall synthesis inhibitor. Examples of such methods include imparting resistance to monofluoroacetic acid (Japanese Patent Laid-open No. 50-113209), resistance to adenine or thymine (Japanese Patent Laid-open No. 57-065198), the method of attenuating urease (Japanese Patent Laid-open No. 52-038088), imparting resistance to malonic acid (Japanese Patent Laid-open No. 52-038088), imparting resistance to benzopyrones or naphthoquinones (Japanese Patent Laid-open No. 56-1889), imparting resistance to HOQNO (Japanese Patent Laid-open No. 56-140895), imparting resistance to α-ketomalonic acid (Japanese Patent Laid-open No. 57-2689), imparting resistance to guanidine (Japanese Patent Laid-open No. 56-35981), imparting sensitivity to penicillin (Japanese Patent Laid-open No. 4-88994), and so forth.

Specific examples of such resistant strains include the following strains:

*Brevibacterium flavum* AJ3949 (FERM BP-2632; Japanese Patent Laid-open No. 50-113209)
*Corynebacterium glutamicum* AJ11628 (FERM P-5736; Japanese Patent Laid-open No. 57-065198)
*Brevibacterium flavum* AJ11355 (FERM P-5007; Japanese Patent Laid-open No. 56-1889)
*Corynebacterium glutamicum* AJ11368 (FERM P-5020; Japanese Patent Laid-open No. 56-1889)
*Brevibacterium flavum* AJ11217 (FERM P-4319; Japanese Patent Laid-open No. 57-2869)
*Corynebacterium glutamicum* AJ11218 (FERM P-4319; Japanese Patent Laid-open No. 57-2869)
*Brevibacterium flavum* AJ11564 (FERM BP-5472; Japanese Patent Laid-open No. 56-140895)
*Brevibacterium flavum* AJ11439 (FERM BP-5136; Japanese Patent Laid-open No. 56-35981)
*Corynebacterium glutamicum* H7684 (FERM BP-3004; Japanese Patent Laid-open No. 04-88994)
*Brevibacterium lactofermentum* AJ11426 (FERM P-5123; Japanese Patent Laid-open No. 56-048890)
*Corynebacterium glutamicum* AJ11440 (FERM P-5137; Japanese Patent Laid-open No. 56-048890)
*Brevibacterium lactofermentum* AJ11796 (FERM P-6402; Japanese Patent Laid-open No. 58-158192)

Examples of microorganisms having L-threonine-producing ability include bacteria belonging to the family Enterobacteriaceae in which one or more activities of L-threonine biosynthesis system enzymes are enhanced. Examples of genes coding for L-threonine biosynthetic enzymes include the aspartokinase III gene (lysC), aspartate semialdehyde dehydrogenase gene (asd), aspartokinase I gene (thrA), homoserine kinase gene (thrB), and threonine synthase gene (thrC) encoded by the threonine operon. Two or more kinds of these genes may be introduced. The genes coding for the L-threonine biosynthetic enzymes may be introduced into an Enterobacteriaceae bacterium with decreased threonine decomposition. Examples of the *Escherichia* bacterium with decreased threonine decomposition include, for example, the TDH6 strain which is deficient in threonine dehydrogenase activity (Japanese Patent Laid-open No. 2001-346578), and so forth.

The activities of the L-threonine biosynthetic enzymes are inhibited by the end product L-threonine, and therefore L-threonine biosynthetic enzymes are preferably modified so as to be desensitized to feedback inhibition by L-threonine when constructing L-threonine producing strains. The above-described thrA gene, thrB gene and thrC gene constitute the threonine operon which has an attenuator structure. The expression of the threonine operon is inhibited by isoleucine and threonine in the culture medium and also inhibited by attenuation. This attenuation can be eliminated or reduced by removing a leader sequence or attenuator in the attenuation region (Lynn, S. P., Burton, W. S., Donohue, T. J., Gould, R. M., Gumport, R. I., and Gardner, J. F. J., Mol. Biol. 194:59-69 (1987); WO02/26993; WO2005/049808).

The native promoter in the upstream region of the threonine operon may be replaced by a non-native promoter (WO98/04715), or the threonine operon may be connected to the repressor and promoter of λ-phage so that expression of the threonine biosynthetic genes is controlled by the repressor and promoter of λ-phage (EP0593792). Furthermore, mutant *Escherichia* bacteria that are desensitized to feedback inhibition by L-threonine can be obtained by selecting strains resistant to α-amino-β-hydroxy isovaleric acid (AHV).

The copy number of the feedback-resistant threonine operon can be increased, or the expression of the modified operon can be increased by connecting it to a potent promoter. The copy number can be increased by using, in addition to amplification using a plasmid, transposon, Mu-phage, or the like so that the operon is transferred onto the chromosome of the host bacterium.

The gene encoding aspartokinase III (lysC) is preferably modified so that the enzyme is desensitized to feedback inhibition by L-lysine. Such a modified lysC gene can be obtained by the method described in U.S. Pat. No. 5,932,453.

L-Threonine-producing bacteria can also be preferably obtained by enhancing expression of genes involved in the glycolytic pathway, TCA cycle, or respiratory chain, or genes that regulate expression of these genes, or genes involved in sugar uptake. Examples of these genes that are effective for L-threonine production include the transhydrogenase gene (pntAB, EP733712B), phosphoenolpyruvate carboxylase gene (pepC, WO95/06114), phosphoenolpyruvate synthase gene (pps, EP877090B), and pyruvate carboxylase gene derived from coryneform bacterium or *Bacillus* bacterium (WO99/18228, EP1092776A).

L-Threonine-producing bacteria can also be preferably obtained by enhancing expression of a gene that imparts L-threonine resistance and/or a gene that imparts L-homoserine resistance, or by imparting L-threonine resistance and/or L-homoserine resistance to the host bacterium. Examples of the genes that impart the above-mentioned resistance include the rhtA gene (Res. Microbiol. 154:123-135 (2003)), rhtB gene (EP0994190A), rhtC gene (EP1013765A), yfiK gene, and yeaS gene (EP1016710A). Exemplary methods for imparting L-threonine resistance to a host bacterium include those described in EP0994190A or WO90/04636.

*E. coli* VKPM B-3996 (U.S. Pat. No. 5,175,107) can also be exemplified as an L-threonine-producing bacterium. The strain VKPM B-3996 was deposited on Nov. 19, 1987 at the Russian National Collection of Industrial Microorganisms (VKPM), GNII Genetika (Russia, 117545 Moscow 1, Dorozhny proezd. 1) under the registration number VKPM B-3996. The VKPM B-3996 strain contains the plasmid pVIC40 (WO90/04636) which was obtained by inserting the threonine biosynthetic genes (threonine operon, thrABC) into a wide host range plasmid vector pAYC32 containing the streptomycin resistance marker (Chistorerdov, A. Y., and Tsygankov, Y. D., Plasmid, 16, 161-167 (1986)). In pVIC40, the threonine operon contains a mutant thrA gene which encodes aspartokinase 1-homoserine dehydrogenase I desensitized to feedback inhibition by threonine.

*E. coli* VKPM B-5318 (EP 0593792B) can also be exemplified as L-threonine-producing bacterium. The VKPM B-5318 strain was deposited in the Russian National Collection of Industrial Microorganisms (VKPM) GNII Genetika on May 3, 1990 under a registration number of VKPM B-5318. The VKPM B-5318 strain is prototrophic with regard to L-isoleucine, and harbors a recombinant plasmid DNA constructed so that the threonine operon, i.e., threonine biosynthesis genes, deficient in the attenuator region, which is an originally contained transcription regulation region, is located downstream from the λ phage-derived temperature-sensitive C1 repressor, PR-promoter, and the gene coding for N-terminal of Cro protein, and the expression of the threonine biosynthesis genes are regulated by the repressor and the promoter derived from λ phage.

In the L-amino acid-producing bacteria, genes involved in sugar uptake, sugar metabolism (glycolytic pathway) and energy metabolism may be amplified in addition to the genes encoding characteristic biosynthesis enzymes.

Examples of the genes involved in sugar metabolism include the genes coding for the enzymes of the glycolytic pathway and sugar uptake genes, and include glucose-6-phosphate isomerase gene (pgi, WO 01/02542), phosphoenolpyruvate synthase gene (pps, EP 877090 A), phosphoglucomutase gene (pgm, WO03/04598), fructose bisphosphate aldolase gene (fbp, WO03/04664), pyruvate kinase gene (pykF, WO 03/008609), transaldolase gene (talB, WO 03/008611), fumarase gene (fum, WO01/02545), phosphoenolpyruvate synthase gene (pps, EP 877090 A), non-PTS sucrose uptake gene (csc, EP 149911 A), and sucrose-assimilating gene (scrAB operon, WO90/04636).

Examples of the genes encoding enzymes involved in energy metabolism include the transhydrogenase gene (pntAB, U.S. Pat. No. 5,830,716) and cytochrome bo-type oxidase gene (cyoB, EP 1070376).

EXAMPLES

Hereafter, the present invention will be specifically explained with reference to the following non-limiting examples.

Reference Example 1

Construction of L-Tryptophan-Producing Bacterium

<1-1> Introduction of serA Gene

The phosphoglycerate dehydrogenase gene (serA) on the pGH5 plasmid (International Patent Publication No. 9408031) was inserted into the genome using the Mud transposon. The pCE1134 plasmid containing MudII1734 (Japanese Patent Laid-open No. 2-109985) was digested with BamHI to remove a DNA fragment containing the lac operon, blunt-ended, and then inserted with a SmaI linker. This plasmid was digested again with SmaI, self-cyclized, and designated pMu1134. A serA-containing DNA fragment was excised from the pGH5 plasmid containing the serA gene of *E. coli* by digestion with ScaI and SalI, blunt-ended, and inserted into the aforementioned pMu1134 at the SmaI site to construct the plasmid pMudserA carrying Mud with the serA gene derived from pGH5 (designated MudserA).

MudserA was transferred to the genome of an L-tryptophan-producing bacterium with desensitized anthranilate synthetase, the SV164 strain (International Patent Publication No. 94/08031), in a conventional manner by using pMudserA which was resistant to kanamycin to obtain the strain L1. The L1 strain was presumed to have MudserA inserted at only one position as a result of Southern hybridization. Moreover, it was revealed that it was inserted at the position 240,950 on the *E. coli* K-12 genome (GenBank Accession No. U00096) by cloning and nucleotide sequencing of the genomic DNA fragment containing MudserA by PCR.

<1-2> Introduction of trp Operon

Then, the copy number of the trp operon was increased by insertion of the trp operon into the genome using a transposon. The trp operon genes were excised from the pGX100 plasmid. pGX100 was obtained by inserting a DNA fragment of the *E. coli* MTR#2 strain having a desensitized trpE gene (U.S. Pat. No. 4,371,614) into pBR313, and a DNA fragment of about 7.6 kb containing the trp operon can be excised by XhoI and SmaI digestion. The DNA fragment containing the trp operon was excised from pGX100 by XhoI and SmaI digestion, blunt-ended, and then inserted into the aforementioned pCE1134 at the SmaI site. A similar DNA fragment containing the trp operon can also be directly cloned from genomic DNA of the *E. coli* MTR#2 strain by PCR using the primers of SEQ ID NOS: 1 and 2. As described above, the pMudtrpG'lac plasmid carrying Mud containing the trp operon genes of the MTR#2 strain (designated MudtrpG'lac) was constructed.

Prior to increasing the copy number by insertion of MudtrpG'lac into the genome, the host strain was made deficient in its ability to utilize lactose for the purpose of using the ability to utilize lactose complementation as a selection marker. The L1 strain was made L-valine resistant by P1 transduction of the ilvG gene derived from the L-threonine-producing bacterium VKPM B-3996 (U.S. Pat. No. 5,175, 107) (refer to International Patent Publication WO2005/103228). The P1 transduction experiment was performed in a conventional manner. The cells were applied onto M9 minimal medium (4 g/L of glucose, 12.8 g/L of Na$_2$HPO$_4$.7H$_2$O, 3 g/L of KH$_2$PO$_4$, 0.5 g/L of NaCl, 1 g/L of NH$_4$Cl, 5 mM MgSO$_4$, 0.1 mM CaCl$_2$, 1 mg/L of thiamine, 20 mg/l of L-Phe, 20 mg/L of L-Tyr, 20 mg/L of L-Met, 3 mg/L of pyridoxine, 20 mg/L of L-Val, 20 mg/L of tetracycline), and the colonies which appeared were determined to be Val-resistant, and this strain was designated L1ValR.

From the ME8581 strain (HfrH(valS←uxuAB):lacZ98::Tn10 relA1 thi-1, deposited at the National Institute of Genetics), P1 transduction of lacZ98::Tn10 into L1ValR was performed in a conventional manner by using the tetracycline resistance of the Tn10 as a marker. The obtained strain lacked lactose utilization ability as expected. Then, in order to obtain a strain lacking lactose utilization ability in which Tn10 is eliminated, a tetracycline sensitive strain, 14-1-lac-tets, was obtained from the transductant strain by replication. The 14-1-lac-tets strain still lacked lactose utilization ability. When the status of Tn10 in this strain was confirmed by Southern hybridization, a band which hybridized to the tet gene was not detected, but a band which hybridized to the IS10 region of Tn10 was detected, and therefore it was determined that IS10 remained on the lacZ gene in this strain.

MudtrpG' lac was transferred to the genome of the 14-1-lac-tets strain in a conventional manner by using pMudtrpG' lac, and a No. 202 strain was obtained by using the complementation of lactose utilization ability as a marker. If the inserted transposon or the gene on the transposon is likely to fall out from the transposon-inserted strain or the transposon, the strain may be subcultured on a nutrient medium, and a strain stably showing kanamycin resistance, lactose utilization ability, etc. may be selected. The No. 202 strain was presumed to have the MudtrpG' lac inserted at only one position as a result of Southern hybridization. Moreover, it was revealed that it was inserted at position 530,249 on the E. coli K-12 genome (GenBank Accession No. U00096) by cloning and nucleotide sequencing of the genomic DNA fragment containing MudtrpG' lac by PCR.

Then, the genes involved in the utilization of sucrose, scrK, scrY, scrA, scrB and scrR, were introduced into the No. 202 strain by P1 transduction, and this strain was designated No. 202 scr (refer to International Patent Publication WO90/04636).

<1-3> Construction of the Plasmid for Disruption of iclR

The iclR fragment was amplified by PCR using Pyrobest DNA Polymerase (Takara Shuzo) according to the method described in the instructions which come with the kit. PCR was performed with the genome of W3110 which had been extracted by using RNA/DNA Maxi Kit (Quiagen), as the template and oligonucleotides of SEQ ID NOS: 3 and 4 as primers. After PCR, the amplified DNA fragment was purified by using Wizard PCR Preps (Promega). After digestion with restriction enzymes EcoRI and HindIII (Takara Shuzo), the purified DNA fragment was subjected to a phenol/chloroform treatment and ethanol precipitation. The digested fragment and pUC18 (Takara Shuzo), which had been digested with the same enzymes and purified, were ligated by using DNA ligation Kit Ver. 2 (Takara Shuzo). Competent cells of JM109 (Takara Shuzo) were transformed with the above ligation reaction solution, and plated on an LB agar plate containing 50 μg/mL of ampicillin (Amp, Meiji Seika) (LB+Amp plate), and colonies were selected at 37° C. The colonies were cultured in LB medium containing 50 μg/mL of Amp at 37° C. in a test tube, and plasmid extraction was performed by using an automatic plasmid extractor, PI-50 (Kurabo Industries).

The obtained plasmid pUCiclR was digested with EcoO65I (Takara Shuzo), then blunt-ended and ligated by using BKL Kit (Takara Shuzo). JM109 was transformed with the ligation solution, colonies were selected, and plasmid extraction was performed as described above. The obtained plasmids were digested with EcoRI and HindIII, purified, and then ligated with the temperature-sensitive plasmid pTS1 (obtained by recombining PstI-HindIII fragments of pMAN031 (J. Bacteriol., 162, 1196-1202 (1985), refer to FIG. 1) and pBR322 (Takara Shuzo)) which had been digested with the same enzymes and purified. JM109 was transformed with the above ligation reaction solution, and colonies were selected at 30° C. on an LB+Amp plate. The colonies were cultured in LB medium containing 50 μg/mL of Amp at 30° C. in a test tube, and plasmids were extracted as described above. A plasmid from which a fragment of the objective length could be obtained by digestion with EcoRI and HindIII was used as the plasmid for iclR disruption, pTSΔiclR.

<1-4> Acquisition of iclR-Disrupted Strain

The No. 202 scr strain was transformed with pTSΔiclR, and colonies were selected on an LB+Amp plate at 30° C. The selected strains were cultured at 30° C. overnight in a liquid culture. The culture medium was diluted 10$^{-3}$ times, and inoculated on an LB+Amp plate, and colonies were selected at 42° C. The selected colonies were applied and spread on an LB+Amp plate, and cultured at 30° C. Then, the cells on ⅛ of the plate were suspended in 2 mL of LB medium, and cultured at 42° C. for 4 to 5 hours with shaking. The cells were diluted 10$^{-5}$ times and seeded on an LB plate, and several hundred colonies among those obtained were inoculated onto an LB plate and LB+Amp plate, and growth was confirmed to determine Amp sensitivity or resistance. Colony PCR was performed for ampicillin-sensitive strains by using the oligonucleotides of SEQ ID NOS: 3 and 4 as primers, and a strain with an amplified fragment which was not digested with EcoO65I was obtained as an iclR-deficient strain (No. 202ΔiclR).

Example 1

Production of L-Tryptophan

One loop of glycerol stock of the tryptophan-producing bacterium No. 202ΔiclR was inoculated on an LB-agarose plate medium (1% tryptone, 0.5% yeast extract, 1% sodium chloride, 1.5% agarose), and cultured at 30° C. for 24 hours as a static culture. One loop (about 10 μl) of the cultured cells were inoculated into 50 ml of LB medium (1% tryptone, 0.5% yeast extract, 1% sodium chloride) in a 500-ml Sakaguchi flask, and pre-cultured at 30° C. for 7 to 8 hours with shaking (115 rpm).

The aforementioned pre-culture medium was inoculated in a volume of 1 ml to 300 ml of a seed culture medium having the composition shown in Table 2. The culture was performed at 30° C. for about 14 hours by using a small fermentation tank having a total volume of 1 L with aeration of compressed air sterilized with a sterilization filter at 1 vvm under stirring at 800 rpm. Furthermore, during the culture, the temperature was maintained at 30° C., and pH was maintained at 6.5 with ammonia gas.

TABLE 2

| Composition of the seed culture medium Components | |
|---|---|
| Glucose | 10 g/L |
| KH$_2$PO$_4$ | 1 g/L |

TABLE 2-continued

Composition of the seed culture medium
Components

| | |
|---|---|
| (NH$_4$)$_2$•SO$_4$ | 2.5 g/L |
| MgSO$_4$•7H$_2$O | 0.5 g/L |
| FeSO$_4$•7H$_2$O | 10 mg/L |
| MnSO$_4$•4H$_2$O | 10 mg/L |
| Soybean hydrolysate | 0.4 g/L |
| L-Methionine | 50 mg/L |
| L-Phenylalanine | 125 mg/L |
| L-Tyrosine | 125 mg/L |
| Vitamin B1 | 5 mg/L |
| Pyridoxine | 30 mg/L |
| GD-113 | 0.05 ml/L |

A medium was obtained by adding methylcellulose (MC, Wako Pure Chemical Industries, Co., Ltd., "Methylcellulose 100 cP") to 300 ml of a main culture medium having the composition shown in Table 3 at a concentration of 1.95 g/L. As a control, 300 ml of the main culture medium without MC was also prepared, and 30 ml of the seed culture medium was inoculated into each. The main culture was performed at 31° C. by using a small fermentation tank having an entire volume of 1 L with aeration of compressed air sterilized with a sterilization filter at 1 vvm with stirring at 800 rpm. Furthermore, during the culture, the temperature was maintained at 31° C., and the pH was maintained at 6.7 with ammonia gas. During the culture, a 700 g/L glucose solution was appropriately fed to control the saccharide concentration in the small fermentation tank to be 5 to 20 g/L.

TABLE 3

Composition of the main culture medium
Components

| | |
|---|---|
| Glucose | 15 g/L |
| KH$_2$PO$_4$ | 1 g/L |
| (NH$_4$)$_2$ SO$_4$ | 1 g/L |
| Soybean hydrolysate | 0.75 g/L |
| NaCl | 0.5 g/L |
| MgSO$_4$•7H$_2$O | 0.3 g/L |
| CaCl$_2$•2H$_2$O | 14.7 mg/L |
| FeSO$_4$•7H$_2$O | 10 mg/L |
| MnSO$_4$•4H$_2$O | 7.5 mg/L |
| L-Methionine | 0.3 g/L |
| L-Phenylalanine | 1 g/L |
| L-Tyrosine | 1 g/L |
| Vitamin B1 | 5 mg/L |
| Pyridoxine | 36.5 mg/L |
| NH$_4$Cl | 3.13 g/L |
| KOH | 1 g/L |
| GD-113 | 0.05 ml/L |

After 49.5 hours of the main culture, the L-tryptophan concentration in the medium was measured. Yield based on saccharide and production rate are shown in Table 4. In Table 4, the results obtained by adding methylcellulose are shown as ratios with respect to the results obtained without adding methylcellulose, which are taken as 1. It was found that if methylcellulose was added, both the yield based on saccharide and production rate were improved compared with those obtained without adding methylcellulose.

TABLE 4

Results of fermentation by main culture

| | Without addition of MC | With addition of MC |
|---|---|---|
| Yield (%) | 1 | 1.26 |
| Production rate (g/L/h) | 1 | 1.33 |

After crystals in the fermentation broth were solubilized in a buffer, the total amount of impurities in the fermentation broth including solubilized crystals were analyzed by HPLC, and it was found that the amount of impurities with addition of methylcellulose was 0.637 based on without addition of methylcellulose, which was taken as 1. Thus, reduction of the total amount of major impurities other than tryptophan was confirmed.

Example 2

Production of L-Phenylalanine

One loop of glycerol stock of a phenylalanine-producing bacterium AJ12741 (FERM BP-4796) was inoculated onto an LB-agarose plate medium (1% tryptone, 0.5% yeast extract, 1% sodium chloride, 1.5% agarose), and cultured at 37° C. for 24 hours as a static culture. One loop (about 10 μl) of the cultured cells were inoculated into 500 ml of LB medium (1% tryptone, 0.5% yeast extract, 1% sodium chloride) and pre-cultured at 37° C. for 7 hours with shaking (115 rpm). The AJ12741 strain was obtained by introducing the pMGAL1 plasmid containing the genes coding for 3-deoxy-D-arabino-heptulosonate-7-phosphate synthase desensitized to feedback inhibition, chorismate mutase-prephenate dehydratase desensitized to feedback inhibition, and shikimate kinase into the Escherichia coli K-12 W3110 strain deficient in the tyrR and tyrA genes (W3110 (tyrR, tyrA)/pMGAL1, Japanese Patent No. 3225597). This strain was deposited on Jun. 11, 1992 under the provisions of the Budapest Treaty in the National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), with a deposit number of FERM P-13000. The original deposit was converted to an international deposit under the provisions of the Budapest Treaty on Sep. 14, 1994 with a deposit number of FERM BP-4796.

The aforementioned pre-culture medium was inoculated in a volume of 1 ml to 300 ml of a seed culture medium having the composition shown in Table 5. The culture was performed at 37° C. for about 14 hours by using a small fermentation tank having a total volume of 1 L with aeration of compressed air sterilized with a sterilization filter at 1 vvm with stirring at 800 rpm. Furthermore, during the culture, the temperature was maintained at 37° C., and pH was maintained at 6.5 with ammonia gas.

TABLE 5

Composition of seed culture medium
Components

| | |
|---|---|
| Glucose | 20 g/L |
| KH$_2$PO$_4$ | 1 g/L |
| (NH$_4$)$_2$ SO$_4$ | 8 g/L |

TABLE 5-continued

| Composition of seed culture medium Components | |
|---|---|
| MgSO$_4$•7H$_2$O | 1 g/L |
| FeSO$_4$•7H$_2$O | 10 mg/L |
| MnSO$_4$•4H$_2$O | 10 mg/L |
| Soybean hydrolysate | 0.3 g/L |
| L-Tyrosine | 300 mg/L |

A medium was obtained by adding methylcellulose (MC, Wako Pure Chemical Industries, Co., Ltd., "Methylcellulose 100 cP") to 300 ml of a main culture medium having the composition shown in Table 6 at a concentration of 0.5 g/L. As a control, 300 ml of the main culture medium not added with MC was also prepared, and 30 ml of the seed culture medium was inoculated into each. The main culture was performed at 37° C. by using a small fermentation tank having a total volume of 1 L with aeration of compressed air sterilized with a sterilization filter at 1 vvm under stirring at 800 rpm. Furthermore, during the culture period, the temperature was maintained at 37° C., and pH was maintained at 7.0 with ammonia gas. During the culture, a 700 g/L glucose solution was appropriately fed to control the saccharide concentration in the small fermentation tank to be 0 to 10 g/L. After 21 hours of the culture, 7 g of L-phenylalanine was added to the fermentation tank.

TABLE 6

| Composition of main culture medium Components | |
|---|---|
| Glucose | 20 g/L |
| KH$_2$PO$_4$ | 1 g/L |
| (NH$_4$)$_2$SO$_4$ | 5 g/L |
| Soybean hydrolysate | 0.5 g/L |
| MgSO$_4$•7H$_2$O | 1 g/L |
| FeSO$_4$•7H$_2$O | 10 mg/L |
| MnSO$_4$•4H$_2$O | 10 mg/L |
| L-Tyrosine | 1 g/L |

TABLE 6-continued

| Composition of main culture medium Components | |
|---|---|
| KOH | 0.8 g/L |
| GD-113 | 0.05 ml/L |

After 46 hours of the main culture, the L-phenylalanine concentration in the medium was measured. Yield based on saccharide and production rate are shown in Table 7. In Table 7, the results obtained by adding methylcellulose are shown as ratios with respect to the results obtained without adding methylcellulose, which are taken as 1. It was found that if methylcellulose was added, both the yield based on saccharide and production rate were improved compared with those obtained without adding methylcellulose.

TABLE 7

Results of fermentation by main culture

| | Without addition of MC | With addition of MC |
|---|---|---|
| Yield (%) | 1 | 1.07 |
| Production rate (g/L/h) | 1 | 1.08 |

INDUSTRIAL APPLICABILITY

According to the present invention, in a method for producing an L-amino acid by fermentation using a microorganism having L-amino acid producing ability, it is possible to improve productivity of the L-amino acid and/or to reduce impurities in crystals of the L-amino acid precipitated in the medium. Improvement of productivity of the L-amino acid include improvement in yield based on saccharide and/or improvement in production rate.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid by fermentation comprising
A) culturing a microorganism which is able to produce the L-amino acid in a liquid medium so that the L-amino acid precipitates into the medium, wherein the medium contains 10 mg/L or more of a polymer selected from the group consisting of a water-soluble cellulose derivative, a water-soluble polyvinyl compound, a polar organic solvent-soluble polyvinyl compound, a water-soluble starch derivative, an alginic acid salt, and a polyacrylic acid salt, wherein said water-soluble cellulose derivative is selected from the group consisting of carboxymethylcellulose, methylcellulose, sodium carboxymethylcellulose, hydroxypropylcellulose, and hydroxypropylcellulose phthalate; and wherein said water-soluble starch derivative is selected from the group consisting of hydroxypropyl starch and gelatin; and
B) collecting the L-amino acid from the medium or the microorganism,
wherein said L-amino acid is selected from the group consisting of L-tryptophan, L-phenylalanine, L-tyrosine, L-isoleucine, L-leucine and L-valine, and
wherein the microorganism can accumulate the amino acid in an amount of 10.6 g/L or more in the case of L-tryptophan fermentation, 27.4 g/L or more in the case of L-phenylalanine fermentation, 0.38 g/L or more in the case of L-tyrosine fermentation, 41.2 g/L or more in the case of L-isoleucine fermentation, 23.8 g/L or more in the case of L-leucine fermentation, or 57.5 g/L or more in the case of L-valine fermentation.

2. The method according to claim 1, wherein the water-soluble polyvinyl compound or polar organic solvent-soluble polyvinyl compound is selected from the group consisting of polyvinylpyrrolidone, polyvinyl alcohol, and polyvinylacetal diethylaminoacetate; and wherein the alginic acid salt is sodium arginate; and wherein the polyacrylic acid salt is sodium polyacrylate.

3. The method according to claim 1, wherein the microorganism is a bacterium belonging to the family Enterobacteriaceae or a coryneform bacterium.

4. The method according to claim 3, wherein said bacterium belongs to the genus *Escherichia* or the genus *Pantoea*.

5. The method according to claim 4, wherein said bacterium is *Escherichia coli*.

6. The method according to claim 1, wherein the polymer is methylcellulose, and the liquid medium contains 1 g/L or more of methylcellulose.

7. The method according to claim 1, wherein said L-amino acid is L-phenylalanine.

8. A method for producing a lower alkyl ester of α-L-aspartyl-L-phenylalanine, comprising producing L-phenylalanine by the method according to claim 7 and synthesizing the lower alkyl ester of α-L-aspartyl-L-phenylalanine from aspartic acid or its derivative and the L-phenylalanine.

9. The method according to claim 8, further comprising
A) esterifying L-phenylalanine to generate a lower alkyl ester of L-phenylalanine,
B) condensing the lower alkyl ester of L-phenylalanine with N-acyl-L-aspartic anhydride,
C) separating the lower alkyl ester of N-acyl-α-L-aspartyl-L-phenylalanine from the reaction mixture, and
D) hydrogenating the lower alkyl ester of N-acyl-α-L-aspartyl-L-phenylalanine to generate the lower alkyl ester of α-L-aspartyl-L-phenylalanine.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
gggttaattg tttttctgcg                                               20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
cgcatctcga ctgcacggtg                                               20
```

-continued

```
<210> SEQ ID NO 3
<211> LENGTH: 27
<212> TYPE: DNA
<213> ORGANISM: Artificial
<220> FEATURE:
<223> OTHER INFORMATION: primer

<400> SEQUENCE: 3
gccgaattca agtgtgtgaa gtgtatg                                    27

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4
gccaagcttc cgacacgctc aacccag                                    27
```